United States Patent [19]

Hamilton

[11] Patent Number: 4,666,908

[45] Date of Patent: May 19, 1987

[54] 5-SUBSTITUTED PYRAZOLO[4,3-D]PYRIMIDINE-7-ONES AND METHODS OF USE

[75] Inventor: Harriet W. Hamilton, Chelsea, Mich.

[73] Assignee: Warner-Lambert Company, Morris Plains, N.J.

[21] Appl. No.: 720,437

[22] Filed: Apr. 5, 1985

[51] Int. Cl.$^4$ .................. A61K 31/415; C07D 471/04
[52] U.S. Cl. ..................... 514/229; 514/234; 514/258; 544/118; 544/262
[58] Field of Search ............... 544/262, 118; 514/258, 514/234, 229

[56] References Cited

U.S. PATENT DOCUMENTS 3,165,520  1/1965  Schmidt ........................... 544/262
3,939,161  2/1976  Ratajczyk ......................... 544/118

FOREIGN PATENT DOCUMENTS 2549834  1/1985  France ............................. 514/258

OTHER PUBLICATIONS

Synthesis, p. 727 (1981).
Bull. Chem. Soc. Japan, 52 (1), 208 (1979).

*Primary Examiner*—Sam Rosen
*Assistant Examiner*—Robert Benson
*Attorney, Agent, or Firm*—Joan Thierstein

[57] ABSTRACT

The present invention relates to novel 5-substituted pyrazolo[4,3-d]pyrimidine-7-one compounds, and compositions, methods of use and processes to make therefor. The novel compounds are useful in the treatment of cardiovascular disorders, such as heart failure or cardiac insufficiency. The novel compounds bind adenosine receptors and selectively inhibit phosphodiesterase.

31 Claims, No Drawings

5-SUBSTITUTED PYRAZOLO[4,3-D]PYRIMIDINE-7-ONES AND METHODS OF USE

BACKGROUND OF THE INVENTION

The present invention provides novel 5-substituted pyrazolo[4,3-d]pyrimidine-7-one compounds. The structurally novel class of compounds contain a ring system numbered clockwise starting with the nitrogen in the diazole substitutent nearest the pyrimidinone ring fused thereto as shown by Formula XL.

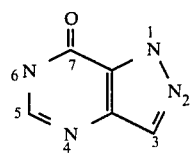

In particular, this invention relates to a combination of substituents on the ring system XL in the one, three, and five position not hitherto known referred to above as 5-substituted pyrazolo[4,3-d]pyrimidine-7-one compounds.

The present invention also relates to novel methods for the synthesis and use of the novel 5-substituted pyrazolo[4,3-d]pyrimidine-7-one compounds disclosed herein. The disclosure particularly relates to the novel compounds for use in the treatment of caridovascular disorders, such as heart failure, or cardiac insufficiency. The novel compounds are found to bind to an adenosine receptor and thus function as antagonists to adenosine or adenosine receptor agonists. Of special interest is the selective inhibition of phosphodiesterase by the novel compounds of the present invention.

Various references disclose compounds having the pyrazolo[4,3-d]pyrimidine-7-one ring system shown by Formula XL. For Example, 1,3-dimethyl-1H-pyrazolo[4,3-d]pyrimidine-7-(6H)-ones useful as anticonvulsants, sedatives, and antiinflammatory and gastric antisecretory agents are disclosed in U.S. Pat. No. 3,939,161 assigned to Abbott Laboratories. However, the disclosed pyrazolo[4,3-d]pyrimidine-7-(6H)-one is limited at the five position on the ring to hydrogen, $C_1$–$C_4$ alkyl, $C_1$–$C_4$ haloalkyl, morpholinomethyl, piperidinomethyl, methoxymethyl, N-methylpiperazinomethyl, benzylthiomethyl, carbethoxy or p-chlorophenoxymethyl.

In Liebigs. Ann. Chem., 7131, 149 (1968) a synthesis of 1-phenyl-5-substituted pyrazolo[4,3-d]pyrimidine-7-ones is taught where the substituent at the five position is methyl, phenyl, benzyl, paramethylbenzyl, naphthyl, cyanoalkyl, or ethoxyethyl. The synthesis does not include any compounds which do not require a phenyl group in the one position. Further, no utility is taught.

Of less interest are compounds having the 3,4-d ring system and shown by the Formula XX

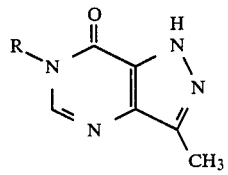

as disclosed in Synthesis, p. 727 (1981) and shown by the Formula XXX

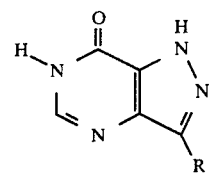

as disclosed in Bull. Chem. Soc. Japan, 52(1), 208 (1979).

None of the compounds as disclosed and discussed above teach the novel compounds of the present invention having the present combination of substituents on the ring system of Formula XL.

SUMMARY OF THE INVENTION

The present invention relates to a novel compound of Formula I

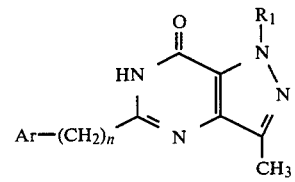

wherein $R_1$ is lower alkyl of from one to six carbons, inclusive, lower alkylene of from one to six carbons, inclusive, lower hydroxyalkyl of from one to six carbons, inclusive, lower hydroxyalkylene of from two to six carbons, inclusive, lower aminoalkyl of from one to six carbons, inclusive, or lower aminoalkylene of from two six carbons, inclusive; n is 0-4; and Ar is

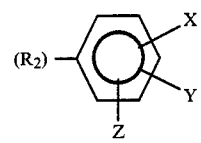

or 2, 3, or 4-pyridyl wherein X, Y, and Z are independently (1) hydrogen; (2) lower alkyl of from one to six carbons, inclusive; (3) halogen; (4) hydroxyl; (5) lower alkoxy of from one to six carbons, inclusive; (6) nitro; (7) amino; (8) NR'R" wherein R' and R" are each independently (a) hydrogen or (b) lower alkyl of from one to six carbons, inclusive, optionally substituted by (i) amino, (ii) morpholino, or (iii) cycloalkyl of from five to seven carbons, inclusive; (9) sulfonyl; or (10) —SO$_2$NR'R" wherein R' and R" are as defined above with the proviso that not all of X, Y, and Z can be nitro, amino, or NR'R" at once, or a pharmaceutically acceptable salt thereof.

A compound of Formula I may exist in one of two tautomers as shown by the formula $I_1 \rightleftarrows I_2$.

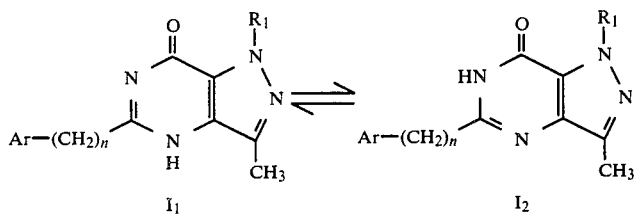

The novel compounds of the present invention having the Formula I are two embodiments, i.e., one wherein Ar if $R_2$ and the second wherein Ar is 2-, 3-, or 4-pyridyl.

The preferred embodiment is a compound of Formula I wherein Ar is $R_2$, wherein $R_2$ is as defined above. Within the preferred embodiment is a more preferred embodiment of Formula I wherein $R_1$ is ethyl or methyl and n is 0 or 1. The most preferred embodiments are a compound of Formula I wherein $R_1$ is methyl, n is 1, and Ar is phenyl, i.e., 1,3-dimethyl-5-benzyl-pyrazolo[4,3-d]pyrimidine-7-one, or a pharmaceutically acceptable salt thereof; a compound of Formula I wherein Ar is 4-chlorophenyl, n is 0, $R_1$ is methyl; i.e., 1,3-dimethyl-5-[4-chlorophenyl]pyrazolo[4,3-d]pyrimidine-7-one or a pharmaceutically acceptable salt thereof; and a compound of Formula I wherein Ar is phenyl, $R_1$ is ethyl, n is 0; i.e., 1-ethyl-3-methyl-5-[4-[N-2-(dimethylamino)ethyl]benzenesulfonamide]-pyrazolo[4,3-d]pyrimidine-7-one or a pharmaceutically acceptable salt thereof.

The present invention also relates to a pharmaceutical composition comprising a therapeutically effective amount of a compound of the above Formula I with a pharmaceutically acceptable carrier and to a method of treating mammals, including humans, by administering to such mammals having a need for the treatment an effective amount of a compound of Formula I as defined above.

DETAILED DESCRIPTION OF THE INVENTION

In the compounds of the Formula I, the term lower alkyl of from one to six carbons, inclusive, means a straight or branched alkyl group, such as, for example, methyl, ethyl, propyl, butyl, amyl, hexyl, and isomers thereof. The term alkylene of from two to six carbons, inclusive, means a straight or branched alkylene group, such as, for example, ethylene, propylene, butylene, amylene, hexylene, and isomers thereof. Hydroxyalkyl of from one to six carbons, inclusive, means alkyl as defined above having a hydroxy substituent. hydroxyalkylene of from two to six carbons, inclusive, means alkylene as defined above having an hydroxy substituent. Likewise, aminoalkyl and aminoalkylene are alkyl or alkylene as defined above having an amino substituent. No limitation as to the location of the substituent hydroxy or amino is included.

The compounds of Formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids, such as hydrochloric acid, sulfuric acid, and the like; and organic acids, such as ethanesulfonic acid, benzenesulfonic acid, p-toluenesulfonic acid, and the like, giving the hydrochloride, sulfamate, ethanesulfonate, benzenesulfonate, p-toluenesulfonate salts, respectively.

Certain compounds of this invention, e.g., those with hydroxyl-bearing or amino-bearing $R_1$, and those lower alkyl of from one to six carbons, inclusive, optionally substituted by amino, morpholine, or cycloalkyl of from five to seven carbons, inclusive, which are so distributed, have asymmetric carbon atoms and such compounds can exist as enantiomers or diastereomers. Thus, all names and representations of compounds as used herein shall include all such isomers and racemic mixtures thereof.

Generally, compounds of Formula I are conveniently synthesized by methods shown in Scheme I and Scheme II Scheme I

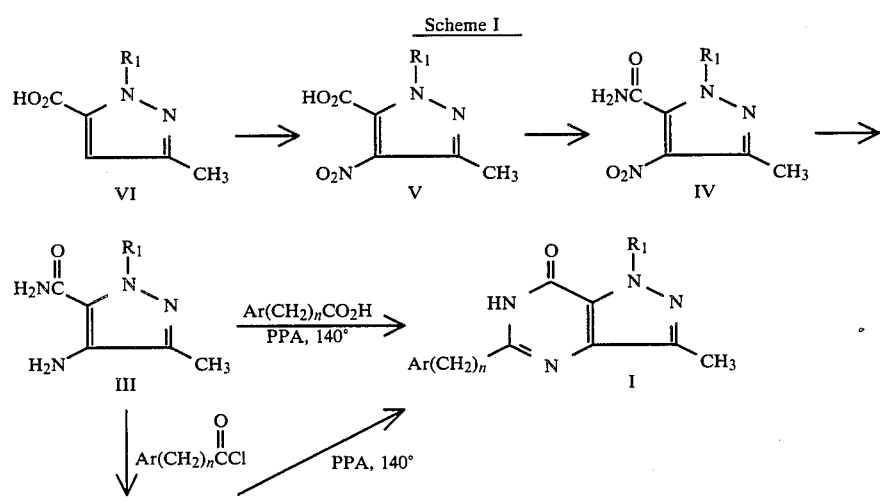

Scheme I -continued

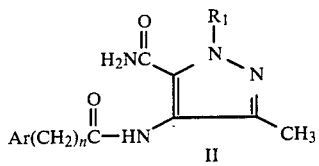

Scheme II

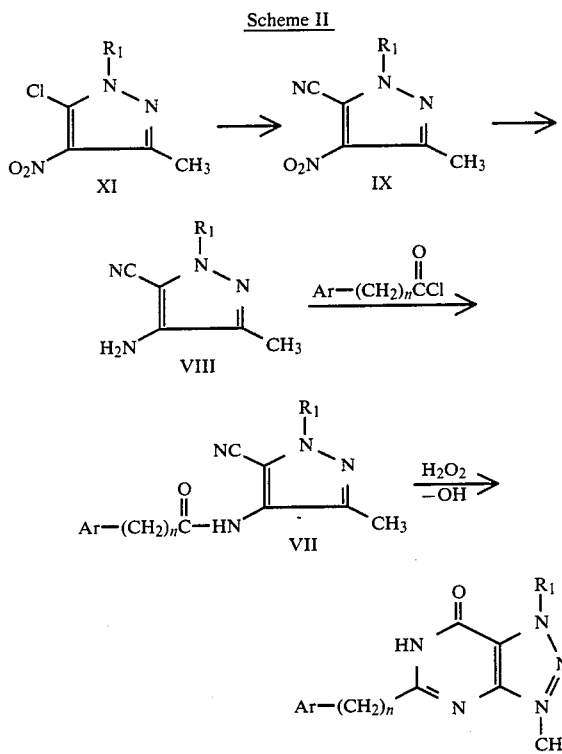

In scheme I the substituted pyrazole of Formula VI; prepared by methods shown in U.S. Pat. No. 3,553,209, is treated with a mixture of sulfuric acid and fuming nitric acid at a temperature of about 80°-100° C. to effect nitration. The amide of Formula IV is synthesized from the acid in the usual manner by treating with thionyl chloride followed by pouring the resulting acid chloride into icy ammonium hydroxide. This nitroamide pyrazole is converted to the amine of Formula III by catalytic hydrogenation utilizing Raney nickel as a catalyst using conditions appropriate for hydrogenation. The substituted pyrazolo-aminoamide of Formula III can then be converted to the product in one of two ways: Stirring with the approriately substituted carboxylic acid in polyphosphoric acid at a temperature of about 140° C. for 4 to 24 hours to obtain the compound of Formula I; alternatively it can be treated first with the appropriately substituted acid chloride in an inert solvent such as methylene chloride in the presence of base to afford the bisamide of Formula II, which is then cyclized with polyphosphoric acid to give the compound of Formula I.

In Scheme II, the substituted nitrochloropyrazole of Formula XI; also prepared by method shown in U.S. Pat. No. 3,553,209, is treated with potassium cyanide to give the nitro-cyanopyrazole of Formula IX, followed by reduction of the nitro group to an amine of Formula VIII by catalytic hydrogenation using Raney nickel as a catalyst. This substituted cyanoamino-pyrazole of Formula VIII is stirred with the appropriately substituted acid chloride in an inert solvent in the presence of a base to afford the cyanopyrazolo-amide of Formula VII, which can be cyclized by treatment with basic hydrogen peroxide at an elevated temperature of from about 80° to 100° C. to give the final compound of Formula I.

The products of the reactions described herein are isolated by conventional means such as extraction, distillation, crystallization, chromatography, and the like.

The acid addition salts of the Formula I compounds are prepared by reacting the amino base with the stoichometric equivalent of the acid corresponding to the pharmacologically acceptable acid addition salt.

The compounds of this invention may also exist in hydrated or solvated forms.

DESCRIPTION OF THE PREFERRED EMBODIMENTS

By virtue of the activity determined by the test procedures as described below the compounds of Formula I are useful in treating symptoms in mammals including humans associated with desirable effects recognized as stimulation of the central nervous system, reversing bronchoconstriction, stimulation of the cardiac system, action of cardiotonic agents. A physician or veterinarian of ordinary skill readily determines a subject who is exhibiting symptoms responding to such desirable effects. Regardless of the route of administration selected, the compounds of the present invention are formulated into pharmaceutically acceptable dosage forms by conventional methods known to the pharmaceutical art. The compounds can be administered in such oral unit dosage forms as tablets, capsules, pills, powders, or granules. They also may be administered rectally, vaginally in such forms as suppositories or bougies: they may also be introduced parenterally (e.g., subcutaneously, intravenously, or intramuscularly), using forms known to the pharmaceutical art. They are also introduced directly to an affected area, (e.g., by inhalation). In general, the preferred route of administration is orally.

An effective quantity of the compound is employed in treatment. The dosage regimen for preventing or treating the symptoms as described above by the compounds of this invention is selected in accordance with a variety of factors including the type, age, weight, sex, and medical condition of the mammal, the severity of the symptoms, the route of administration, and the particular compound employed. An ordinarily skilled physician or veterinarian will readily determine and prescribe the effective amount to prevent or arrest the progress of the condition having the symptoms as described herein.

Daily dosages of the compounds of the invention are ordinarily in the area of 0.1 mg/kg to at least 100 mg/kg per dose orally, preferably 1 to 50 mg/kg orally and are given from one to four times daily or as needed. When other forms of administration are employed equivalent doses are administered. When dosages beyond 200 mg/kg are employed, care should be taken with each subsequent dose to monitor possible toxic effects.

PHARMACOLOGICAL EVALUATION

The compounds of Formula I have been found to possess affinity for adenosine receptors (designated $A_1$ for convenience).

Adenosine Receptor Binding - $A_1$ Receptor Affinity (RBA1)

Preparation of Membranes

Whole brain minus cerebellum and brainstem from male Long Evans rats (150–200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000×g (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05 M Tris-HCl buffer pH 7.7 to a concentration of 20 mg/ml original wet tissue weight and used immediately.

Assay Conditions

Tissue homogenate (10 mg/ml was incubated in 0.05 M Tris-Hcl buffer ph 7.7 containing 1.0 nM [$^3$H]-$N^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05 M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding (IC$_{50}$) was determined by nonlinear computer curve fit. The Scatchard plot was calculated by linear regression of the line obtained by plotting the amount of radioligand bound (mmoles/gram of tissue) versus $$\left[ \frac{\text{bound radioligand}}{\text{free radioligand}} \right].$$

Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the log of the $$\left[ \frac{\text{bound radioligand}}{B_{max} - \text{bound radioligand}} \right].$$

The maximal number of binding sites ($B_{max}$) was calculated from the Scatchard plot.

The IC$_{50}$ values (nM) for adenosine $A_1$ receptor affinity is reported in Table 1.

TABLE 1

| | Receptor Binding |
|---|---|
| Example | RBA-1 (nM) |
| 1 | 13,100 |
| 2 | 953 |
| 3 | 237 |
| 4 | 3,090 |
| 5 | 670 |
| 6 | 1,020 |
| 7 | 408 |
| 8 | 417 |
| 9 | 880 |
| 10 | 463 |
| 11 | 385 |
| 12 | 1,540 |
| 13 | 1,200 |
| 14 | 10,000 |
| 15 | 887 |
| 16 | 1,920 |
| 17 | 5,430 |
| 18 | 8,500 |
| 19 | 314 |
| 20 | 13,000 |
| 21 | 684 |
| 22 | 8,200 |

Phosphodiesterase (PDE) Inhibition

Isolation of Multiple Molecular Forms of Phosphodiesterase

The method of Thompson, et al (Thompson, W. J., Terasaki, W. L., Epstein, P. M., Strada, S. J., *Adv. Cyclic Nucleotide Res.*, 10:69–92, 1979), with minor modifications, was used to isolate phosphodiesterases from vascular smooth muscle. Bovine coronary arteries (right, anterior descending, and left circumflex arteries) from hearts obtained from a local slaughterhouse were used for these studies. Arteries from two hearts were used for each isolation. Hearts were kept on ice and the arteries were dissected within two hours after the animals were sacrificed. After removing all fat and connective tissue, the arteries were everted, cut into cubes with a single edge razor blade and homogenized with a Brinkman Polytron three times at a rheostat setting of 10.0 in four volumes of the PDE isolation buffer (10 mM Tris-HCl/pH 7.5, 2 mM MgCl$_2$, and 1 mM dithiothreitol). The resulting homogenate was sonicated (30 sec/ml homogenate) and then centrifuged at 30,000 xg for 20 minutes. This and all subsequent procedures were performed at 4° C. The resulting supernatant was filtered through four layers of gauze, and applied to a DEAE-cellulose column (30×1.5 cm), prepared as described by Cheung (Cheung, W. Y., *Biochim. Biophys. Acta*, 191:303–315, 1969), and equilibrated with freshly prepared 70 mM sodium acetate/5 mM 2-mercaptoethanol (pH 6.5). The column was then washed with 2-3 bed volumes of sodium acetate/2-mercaptoethanol, after which the phosphodiesterases were eluted from the column using a continuous 70–1,000 mM sodium acetate gradient (pH 6.5, containing 5 mM 2-mercaptoethanol; total volume 400 ml). The flow rate was approximately equal to 25 ml/hr. Eight ml fractions were collected and assayed for cyclic AMP- and cyclic GMP-phosphodiesterase activity in the presence and absence of 0.1 units of calmodulin and 10 mM $CaCl_2$. Appropriate fractions were pooled and dialyzed against 70 mM sodium acetate/5 mM 2-mercaptoethanol for 20 hours.

Following complete separation, the combined phosphodiesterase fractions were concentrated to 14% of the original volume using an Amicon ultrafiltration cell fitted with a UM-10 membrane, according to the method of Wells, et al (Wells, J. N., Baird, C. E., Wu, Y. J., Hardman, J. G., *Biochim. Biophys. Acta*, 384:430-442, 1975). Following concentration, the protein was then diluted to 65% with ethylene glycol monoethyl ether, and stored at −20° C. No significant change in hydrolytic activity was observed with storage up to six weeks.

Measuring Phosphodiesterase Activity

Phosphodiesterase activity was measured as described previously (Weishaar, P. E., Quade, M., Boyd, D., Schenden, J., Mark, S. S., Kaplan, H. R., *Drug Devel. Res.*, 3:517-534, 1983), in a reaction medium containing 40 mM Tris-HCl (pH 8.0), 5 mM MgCl and 4 mM 2-mercaptoethanol. Unless otherwise noted, the concentration of substrate ($^3$H-cyclic AMP or $^3$H-cyclic GMP) was 1.0 μM. All agents examined were dissolved in dimethyl sulfoxide (DMSO). Final concentration of the reaction medium was either 2.5% (cardiac and platelet studies) or 1.25% (smooth muscle studies). This concentration of DMSO produced an approximately 10% inhibition of enzyme activity.

TABLE 2

| Example | Type 1 Phosphodiesterase | | Type 3 Phosphodiesterase |
|---|---|---|---|
| | % Inhibition of hydrolysis of 3H-cAMP at $10^{-5}$M | % Inhibition of hydrolysis of 3H-cGMP at $10^{-5}$M | % Inhibition of hydrolysis of 3H-cAMP at $10^{-5}$M |
| 1 | 80 | 71 | 23 |
| 2 | 5 | 13 | 20 |
| 3 | 33 | 19 | 55 |
| 9 | 16 | 6 | 1 |
| 10 | 12 | 1 | −9 |
| 11 | 19 | 15 | 32 |
| 12 | 6 | 9 | 33 |
| 13 | 30 | 18 | 50 |
| 15 | 5 | 3 | 0 |
| 18 | 7 | 5 | 7 |
| 19 | 16 | 12 | 5 |
| 4 | 6 | 4 | 3 |
| 5 | 29 | 29 | 56 |
| 6 | 6 | 14 | 35 |
| 7 | 7 | 11 | 13 |
| 8 | 14 | 15 | 15 |
| 16 | 10 | 17 | 17 |
| 17 | 15 | 26 | 17 |

The usefulness of the compounds of the present invention as cardiotonic agents is demonstrated by their effectiveness if standard pharmacological test procedures, for example, in causing a significant increase in the myocardial contractility in the pentobarbital-anesthetized dog with low or minimal changes in heart rate and blood pressure. This test procedure is described in the following paragraphs.

Test for In Vivo Myocardial Inotropic Activity in Anesthetized Dog (CVAD)

This screen consists of determining the effects of increasing intravenous doses of compound on mycardial contractility (dP/dt max of left ventricular blood pressure), heart rate, and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 to 1.0 N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 mg/kd over a period of one minute.

When tested by the above-described Anesthetized Dog Procedure, the compounds of the present invention, for example, compound Ia of Example 1, when administered intravenously at about 0.01 to 0.31 mg/kg cause dose related significant increases in cardiac contractility with only low or minimal changes in heart rate and a moderate reduction in blood pressure. Accordingly, the compounds of the present invention are also useful as antihypertensive agents.

The results are summarized in the following table.

TABLE 3

| | | Percent Change | | |
|---|---|---|---|---|
| Example | Dose (mg/kg) | Myocardial Contractility | Heart Rate | Blood Pressure |
| 1 | 0.00 | | | |
| | 0.10 | +8 | +2 | +1/0 |
| | 0.31 | +12 | +3 | 0/−1 |
| | 1.00 | +23 | +6 | −3/−5 |
| | 3.10 | +42 | +14 | −4/−7 |
| | 10.00 | +95 | +38 | −17/−25 |
| 2 | 0.00 | | | |
| | 0.10 | +4 | +1 | 0 |
| | 0.31 | +7 | +1 | +1/0 |
| | 1.00 | +53 | +28 | +4/6 |
| | 3.10 | +121 | +49 | +5/+6 |
| 3 | 0.00 | | | |
| | 0.10 | +12 | +4 | +2 |
| | 0.30 | +20 | +7 | +2 |
| | 1.00 | +47 | −1 | +2 |
| | 3.10 | +91 | +16 | +8 |
| 4 | 0.00 | | | |
| | 0.10 | +2 | 0 | 0/0 |
| | 0.31 | +7 | +1 | −1/−1 |
| | 1.00 | +27 | +4 | 0/−1 |
| | 3.10 | +55 | +9 | −1/−5 |
| 5 | 0.00 | | | |

TABLE 3-continued

| Example | Dose (mg/kg) | Percent Change Myocardial Contractility | Heart Rate | Blood Pressure |
|---|---|---|---|---|
| | 0.10 | +10 | +7 | 2 |
| | 1.00 | +77 | +43 | 1 |
| | 3.10 | +100 | +50 | 1 |
| 6 | 0.00 | | | |
| | 0.10 | +4 | −1 | +5/+5 |
| | 0.31 | +3 | −4 | +8/+8 |
| | 1.00 | +20 | 7 | +12/+12 |
| | 3.10 | +45 | 37 | 0/−1 |
| 8 | 0.00 | | | |
| | 0.10 | +7 | +5 | −1 |
| | 0.30 | +10 | +5 | 0 |
| | 1.00 | +20 | +6 | +3 |
| | 3.10 | +22 | +10 | +3 |
| | 10.00 | +82 | | |
| 9 | 0.00 | | | |
| | 0.10 | +4 | 1 | +3/+3 |
| | 0.31 | +5 | 0 | +3/+3 |
| | 1.00 | +4 | −3 | +3/+4 |
| | 3.10 | +2 | 1 | +3/+5 |
| 11 | 0.00 | | | |
| | 0.10 | +9 | +1 | 1/1 |
| | 0.31 | +17 | +3 | 5/3 |
| | 1.00 | +25 | +5 | 1/0 |
| | 3.10 | +66 | +15 | −7/−11 |
| 12 | 0.00 | | | |
| | 0.10 | −1 | −8 | 4/−1 |
| | 0.31 | −19 | −10 | −11/−7 |
| | 1.00 | −12 | −8 | −9/−6 |
| 13 | 0.00 | | | |
| | 0.10 | 6 | 2 | −2 |
| | 0.30 | 5 | 4 | −4 |
| | 1.00 | −7 | −3 | −7 |
| | 3.10 | 6 | −3 | −12 |
| | 10.00 | 101 | | |
| 14 | 0.00 | | | |
| | 0.10 | 2 | 2 | −1/0 |
| | 0.31 | 4 | 4 | −2/−2 |
| | 1.00 | 10 | 14 | −2/−3 |
| | 3.10 | 34 | 27 | −5/−8 |
| 15 | 0.00 | | | |
| | 0.10 | 8 | 7 | 1/2 |
| | 0.31 | 10 | 7 | −1/−1 |
| | 1.00 | 13 | 9 | −1/−1 |
| | 3.10 | 13 | 12 | 1/2 |
| 16 | 0.00 | | | |
| | 0.10 | 2 | 1 | −1/−1 |
| | 0.31 | −1 | −1 | 1/3 |
| | 1.00 | −1 | −2 | 1/2 |
| 22 | 0.00 | | | |
| (Test 1) | 0.01 | 11 | −1 | 1/0 |
| | 0.03 | 12 | −1 | 0/−1 |
| | 0.10 | 17 | −4 | −2/−5 |
| | 0.30 | 6 | −10 | −7/−12 |
| | 1.00 | 14 | −12 | −3/−6 |
| (Test 2) | 0.00 | | | |
| | 0.01 | −12 | −14 | 0/−2 |
| | 0.03 | −13 | −17 | −1/−4 |
| | 0.10 | −15 | −21 | −1/−4 |
| | 0.31 | −14 | −22 | −2/−4 |
| | 1.00 | 2 | −11 | −2/−5 |
| 23 | 0.00 | | | |
| | 0.01 | +5 | +1 | 2/2 |
| | 0.31 | +15 | +3 | 3/4 |
| | 1.00 | +22 | +6 | −2/−3 |

The operation of this invention is further elaborated by the representative examples below.

EXAMPLE 1

1,3-Dimethyl-5-benzylpyrazolo[4,3-d]pyrimidine-7-one

The compound was prepared as in Example 6A using 1.11 g of 1,3-dimethyl-5-cyano-pyrazole-4-N-benzylcarboxamide, 0.26 g sodium hydroxide and 1 ml 30% $H_2O_2$.

Analysis as: $C_{14}H_{14}N_4O \cdot \frac{1}{8}H_2O$: Calcd: C, 61.24; H, 5.97; N, 20.41; Found: C, 61.54; H, 5.64; N, 20.18.

The starting material was prepared as in Example 6A using phenylacetic acid chloride, mp 184°–185° C.

EXAMPLE 2

1,3-Dimethyl-5-(4-pyridyl)-pyrazolo[4,3-d]pyrimidine-7-one

The compound was prepared as in Example 6B using 5 g of 1,3-dimethyl-4-aminopyrazole-5-carboxamide and 3.99 g isonicotinic acid. After pouring into ice water the aqueous solution was treated with 25% potassium hydroxide to give a percipitate. This was collected and recrystallized to ethanol to give the product, mp 321°–322° C.

Analysis as: $C_{12}H_{11}N_5O$: Calcd: C, 59.74; H, 4.60; N, 29.03; Found: C, 59.45; H, 4.53; N, 28.81

EXAMPLE 3

1-Ethyl-3-methyl-5-(4-pyridyl)pyrazolo[4,3-d]pyrimidine-7-one

The starting bis-amide was prepared as described in Example 4 using 4.78 g of 1-ethyl-3-methyl-4-aminopyrazole-5-carboxamide, 5.06 isonicotanoyl chloride hydrochloride, and 5.74 g triethylamine. This compound was cyclized as in Example 6B using 300 g polyphosphoric acid. The aqueous solution was neutralized with 50% sodium hydroxide, the resulting percipitate collected and then recrystallized in ethanol, mp 257°–260° C.

Analysis as: $C_{13}H_{13}N_5O$: Calcd: C, 61.17; H, 5.13; N, 27.43; Found: C, 60.91; H, 5.15; N, 27.66

EXAMPLE 4

1,3-Dimethyl-5-(3-pyridyl)pyrazolo[4,3-d]pyrimidine-7-one

Two g of 1,3-dimethyl-4-amino-pyrazole-5-carboxamide, 2.31 g nicotinic acid chloride.hydrochloride and 3.03 g triethylamine were combined in chloroform and stirred at reflux for 18 hours. The solution was cooled and washed with water. A percipitate formed in the aqueous layer, which was filtered and dried to give the bis-amide, mp 209°–211° C. An additional crop was isolated by pouring the chloroform solution over ice, then filtering the resulting percipitate, mp 209°–211° C.

The bis-amide was cyclized in 75 g of polyphosphoric acid at 145° C. for four hours. This was poured into rapidly stirred ice water, and then neutralized to pH 7–8 with 50% sodium hydroxide. The resulting percipitate was collected, and recrystallized in ethanol-water to give the product, mp 309°–309.5° C.

Analysis as: $C_{12}N_{11}N_4O \cdot 0.1\ H_2O$: Calcd: C, 59.30; H, 4.64; N, 28.81; Found: C, 59.57; H, 4.91; N, 28.52

EXAMPLE 5

1-Ethyl-3-methyl-5-phenylpyrazolo[4,3-d]pyrimidine-7-one

The starting bis-amide was prepared in an analogous manner to the starting material for Example 6A using 5 g of 1-ethyl-3-methyl-4-amino-pyrazole-5-carboxamide, 4.18 g benzoyl chloride and 3 g of triethylamine, mp 219°–220° C.

This was cyclized as in Example 6B using 5.12 g bis-amide and 150 g polyphosphoric acid. The product was filtered directly from the ice water solution, mp 218°–221° C.

Analysis as: $C_{14}H_{14}N_4O.0.5\ H_2O$: Calcd: C, 63.86; H, 5.74; N, 21.28; Found: C, 64.17; H, 5.48; N, 21.30

EXAMPLE 6- METHOD A (SCHEME 2)

1,3-Dimethyl-5-phenylpyrazolo[4,3-d]pyrimidine-7-one

Two-tenths g of sodium hydroxide was dissolved in 30 ml water and heated to 40° C. Eight-tenths ml of 30% hydrogen peroxide was added, followed by 0.77 g 1,3-dimethyl-5-cyanopyrazole-4-N-phenylcarboxamide. The mixture was heated to 80° for 4.5 hours, then cooled and acidified with glacial acetic acid. A white percipitate formed, which was filtered and recrystalized from ethanol to give the product, 1,3-dimethyl-5-phenylpyrazolo[4,3-d]pyrimidine-7-one, mp 269°–271° C.

Analysis as: $C_{13}H_{12}N_4O.0.25\ H_2O$: Calcd: C, 63.86; H, 5.24, N, 22.91; Found: C, 63.74; H, 5.33; N, 22.74

Starting material for Example 6 - 1,3-dimethyl-5-cyanopyrazole-4-N-phenylcarboxamide One g, 1,3-Dimethyl-4-amino-5-cyanopyrazole and 1 g benzoyl chloride were stirred with 0.71 g triethylamine in methylene chloride for 14 hours. The reaction mixture was washed with 5% aqueous HCl, dried over magnesium sulfate, then concentrated to a pale orange solid. This was recrystallized from chloroform/methanol to yield, 1,3-dimethyl-5-cyanopyrazole-4-N-phenylcarboxamide, mp 212°–213° C.

EXAMPLE 6 - METHOD B (SCHEME 1)

Five g 1,3-dimethyl-4-aminopyrazole-5-carboxamide, and 3.96 g benzoic acid were combined in 50 g polyphosphoric acid at 80° C. Heated to 140° C. for six hours, then cooled, and poured into ice water with rapid stirring. The resulting percipitate was collected and recrystallized in ethanol to give the product 1,3-dimethyl-5-phenylpyrazolo[4,3-d]pyrimidine-7-one, mp 273°–274° C.

Analysis as: $C_{13}H_{12}N_4O.0.5\ H_2O$: Calcd: C, 62.63; H, 4.85; N, 22.48; Found: C, 62.70; H, 4.71; N, 22.41.

EXAMPLE 7

1,3-Dimethyl-5-(4-chlorophenyl)pyrazolo[4,3-d]pyrimidne-7-one 1,3-Dimethyl-5-(4-chlorophenyl)pyrazolo[4,3-d]pyrimidine-7-one was made as in Example 6B using 8 g of 1,3-dimethyl-4-N-(4-chlorophenylcarboxamide)-pyrazole-5-carboxamide in 280 g polyphosphoric acid, mp 314°–316° C.

Analysis as: $C_{13}H_{11}N_4OCl.0.25\ H_2O$: Calcd: C, 55.56; H, 4.26; N, 19.94; Cl, 12.72; Found: C, 55.92; H, 4.15; N, 20.07; Cl, 12.70

The 1,3-dimethyl-4-N-(4-chlorophenylcarboxamide)-pyrazole-5-carboxamide is prepared as in Example 6B however, using 4-chlorobenzoyl chloride for benzoic acid before cyclizing with polyphosphoric acid.

EXAMPLE 8

1,3-Dimethyl-5-(4-methylphenyl)pyrazolo[4,3-d]pyrimidine-7-one

The starting bis-amide was prepared as in Example 4 using 5 g of 1,3-dimethyl-4-amino-pyrazole-5-carboxamide, 5 g p-methylbenzoylchloride, and 3.28 g triethylamine, mp 210°–211° C.

It was cyclized as in Example 43 with 200 g polyphosphoric acid to give the product, mp 271°–272° C.

Analysis as: $C_{14}H_{14}N_4O.0.1\ H_2O$: Calcd: C, 65.66; H, 5.59; N, 21.87; Found: C, 65.71; H, 5.60; N, 21.98

EXAMPLE 9

1,3-Dimethyl-5-(4-nitrophenyl)pyrazolo[4,3-d]pyrimidine-7-one

The bis-amide starting material was prepared as in Example 4 using 10 g of 1,3-dimethyl-4-aminopyrazole-5-carboxamide, 12.04 g p-nitro-benzoyl chloride and 6.55 g triethylamine, mp 283°–285° C. It was cyclized as in Example 6A using 2 g bis-amide, 0.36 g sodium hydroxide, and 1.42 ml 30% hydrogen peroxide to give the product, mp>340° C.

Analysis as: $C_{13}H_{11}N_5O_3.0.25\ H_2O$: Calcd: C, 53.87; H, 4.00; N, 24.17; Found: C, 53.83; H, 3.93; N, 23.87

EXAMPLE 10

1,3-Dimethyl-5-(4-trifluoromethylphenyl)pyrazolo[4,3-d]pyrimidine

The compound is prepared as in Example 6B using 1.75 g of 1,3-dimethyl-4-aminopyrazole-5-carboxamide, 2.16 g p-trifluoromethylbenzoic acid, and 100 g polyphosphoric acid, and recrystallized in ethanol, mp 286°–289° C.

Analysis as: $C_{14}H_{11}N_4OF_3.0.5\ H_2O$: Calcd: C, 53.00, H, 3.81, N, 17.66; Found: C, 52.93; H, 3.99; N, 17.50

EXAMPLE 11

1,3-Dimethyl-5-(4-aminophenyl)pyrazolo[4,3-d]pyrimidine-7-one

The compound was prepared by catalytic reduction of the compound obtained in Example 9 in aqueous base using Raney nickel. After 89% of the theoretical amount of hydrogen was taken up, acetone was added to the reaction mixture, and it was filtered and the acetone removed. It was then taken to pH 6 with 0.1 N HCl, and the resulting percipitate filtered. Recrystallized from ethanol, mp 340°–341° C.

Analysis as: $C_{13}H_{13}N_5O$: Calcd: C, 61.17; H, 5.13; N, 27.43; Found: C, 60.83; H, 4.90, N, 27.22

EXAMPLE 12

1,3-Dimethyl-5-(3-aminophenyl)pyrazolo[4,3-d]pyrimidine-7-one

The compound was prepared as in Example 11 using material from Example 13, mp 287°–289° C.

Analysis as: Calcd: C, 61.17; H, 5.13; N, 27.43; Found: C, 60.83; H, 5.42; N, 27.02

EXAMPLE 13

1,3-Dimethyl-5-(3-nitrophenyl)pyrazolo[4,3-d]pyrimidine-7-one

The starting bis-amide was prepared as in Example 4 using 10 g of 1,3-dimethyl-4-amino-pyrazole-5-carboxamide, 12.04 g m-nitro-benzoylchloride and 6.55 g triethylamine, mp 242°–245° C. This was cyclized as in Example 6A using 10 g bis-amide, 1.98 g sodium hydroxide and 7.1 ml 30% hydrogen peroxide to give the product. This was purified by boiling ethanol, the insoluble protion being the product, mp 334°–336° C.

Analysis as $C_{13}H_{11}N_5O_3$: Calcd: C, 54.74; H, 3.89; N, 24.55; Found: C, 54.49; H, 3.95; N, 24.65

EXAMPLE 14

1,3-Dimethyl-5(2-methoxyphenyl(pyrazolo [4,3-d]-pyrimidine-7-one

The bis-amide was prepared as in Example 4 using 2.0 g of 1,3-dimethyl-4-aminopyrazole-5-carboxamide, 2.21 g of 0-methoxybenzoylchloride, and 1.31 g of triethylamine, mp 217°–219° C. This was cyclized as in Example 4 using 100 g polyphosphoric acid to give the product, mp 222°–223.5° C.

Analysis as: $C_{14}H_{14}N_4O_2$: Calcd: C, 62.21; H, 5.22; N, 20.73; Found: C, 62.48; H, 5.50; N, 20.59

EXAMPLE 15

1,3-Dimethyl-5-(3,4-dichlorophenyl)pyrazolol[4,3-d]-pyrimidine-7one

The compound was prepared as in Example 6B using 7.25 g of 1,3-dimethyl-4-N-(3,4dichlorphenyl) carboxamide pyrazole-5-carboxamide in 300 g polyphosphoric acid, mp. >360° C.

Analysis as: $C_{13}H_{10}N_4OCl_2 \cdot H_2O$: Calcd: C, 47.53; H, 3.70, N, 17.12; Cl, 21.67; Found: C, 47.34; H, 3.52; N, 16.92; Cl, 20.84

1,3-Dimethyl-4-N-(3,4-dichlorophenyl)carboxamidepyrazolo-5-carboxamide is prepared as in Example 6B, however, using 3,4-1-dichlorobenzoyl-chloride for benzoic acid before cyclizing with polyphosphoric acid, mp 270°–272° C.

EXAMPLE 16

1,3-Dimethyl-5-(3,4-dimethoxyphenyl)pyrazolo[4,3-d]pyrimidine-7-one

The compound was prepared as in Example 6B using 5 g of 1,3-dimethyl-4-aminopyrazole-5-carboxamide and 5.91 g of the commercially available 3,4-1-dimethoxy-benzoic acid, mp 259°–260° C.

Analysis as: $C_{15}H_{16}N_4O_3$: Calcd: C, 59.99; H, 5.37; N, 18.66; Found: C, 59.80; H, 5.43; N, 18.29

EXAMPLE 17

1,3-Dimethyl-5-(2,4-dimethoxyphenyl)pyrazolo[4,3-d]-pyrimidine-7-one

The compound was prepared as in Example 6B using 5 g of 1,3-dimethyl-4-aminopyrazole-5-carboxamide and 5.91 g of the commercially available 2,4-dimethoxybenzoic acid, mp 246°–247° C.

Analysis as: $C_{15}H_{16}N_4O_3$: Calcd: C, 59.99; H, 5.37; N, 18.66; Found: C, 59.63; H, 5.42; N, 18.47

EXAMPLE 18

1,3-Dimethyl-5-(2-nitro-4-chlorophenyl)pyrazolo-[4,3-d]pyrimidine-7-one

The starting bis-amide was prepared as in Example 4 using 10 g of 1,3-dimethyl-4-aminopyrazole-5-carboxamide, 11.97 g, 2-nitro-4-chlorobenzoyl chloride, and 6.55 g triethylamine, mp 295°–296° C. The bis-amide as cyclized as in Example 6A using 10.25 g bis-amide, 1.82 g sodium hydroxide, and 7.28 ml 30% hydrogen peroxide to give the product, mp 154°–257° C.

Analysis as: $C_{13}H_{10}N_5O_3Cl$; Calcd: C, 48.84; H, 3.15; N, 21.91; Cl, 11.09; Found: C, 48.19; H, 3.13; N, 21.76; Cl, 11.47

EXAMPLE 19

1,3-Dimethyl-5-(2-amino-4-chlorophenyl)pyrazolo[4,3-d]pyrimidine-7-one

The compound was prepared by catalytic reduction as in Example 11 using material from Example 18. It was recrystallized in ethanol, mp 309°–311° C.

Analysis as: $C_{13}H_{12}N_5OCl \cdot 0.25 H_2O$; Calcd: C, 53.07; H, 4.28; N, 23.80; Cl, 12.05; Found: C, 53.14; H, 4.61; N, 23.81; Cl, 10.75

EXAMPLE 20

1,3-Dimethyl-5-(4-sulfoacid phenyl)pyrazolo[4,3-d]pyrimidine-7-one

The compounds was prepared as in Example 6B using 9 g of 1,3-dimethyl-4-amino-pyrazolo-5-carboxamide and 14 g benzoic-4-sulfonic acid in 900 g polyphosphoric acid. It was purified by recrystallization in 1:1 methanol water, mp >360° C.

Analysis as $C_{13}H_{12}N_4O_4S$: Calcd: C, 48.75; H, 3.78; N, 17.49; S, 10.01; Found: C, 48.61; H, 3.78; N, 17.52; S, 9.84

EXAMPLE 21

1,3-Dimethyl-5[4-(N-2-(dimethylamino)ethylbenenesulfonamide]pyrazolo[4,3-d]pyrimidine-7-one The compound was prepared using material from Example 20. Of this 2.67 g was suspended in DMF, and 1.98 g thionyl chloride added at 0° C. After three hours, 10ml unsymmetrical dimethylethylenediamine was added dropwise. The reaction mixture was allowed to come to room temperature, then heated under reduced pressure. After cooling, a precipitate formed which was filtered away. Further concentration of the filtrate yielded a semisolid which was stirred in ice water. The resulting solid was recrystallized in methanol, mp 236°–8° C.

Analysis as: $C_{17}H_{22}N_6O_3S \cdot 1.5 H_2O$: Calcd: C, 48.91; H, 6.03; N, 20.13; S, 8.21; Found: C, 49.11; H, 6.04; N, 20.02; S, 7.90

EXAMPLE 22

1-Ethyl-3-methyl-5-benzylpyrazolo[4,3-d][pyrimidine-7-one

The starting bis-amide was prepared as in Example 6A using phenylacetic acid chloride and 1-ethyl-3-methyl-4-amino-pyrazole-5-carboxamide, mp 236°–236.5° C. This bis-amide was cyclized using 60 polyphosphoric acid as in Example 6B. The product was recrystallized in ethanol, mp 209°–210° C.

Analysis as: $C_{15}H_{16}N_4O$: Calcd: C, 67.15, H, 6.01, N, 20.88; Found: C, 67.19; H, 5.82; N, 20.64

EXAMPLE 23

1,3-Dimethyl-5-(3,5-dimethoxyphenyl)pyrazolo[4,3-d]-pyrimidine-7-one

The compound was prepared as in Example 6B using the product of 5 g of 1,3-dimethyl-4-aminopyrazole-5-carboxamide and 6.51 g of 3,5-diethoxybenzoyl chloride in methylene chloride with 3.3 g triethylamine. After stirring 20 hours at ambient temperature, washing with water and concentration, the crude material was treated with polyphosphoric acid as described. Recrystallization two times from ethanol yielded the product, mp 255°–256° C.

Analysis as: $C_{15}H_{16}N_4O_3 \cdot 0.5H_2O$: Calcd: C, 58.24; H, 5.54; N, 18.11; Found: C, 58.21; H, 5.43; N, 17.99

EXAMPLE 24

1,3-Dimethyl-5-(3-methoxyphenyl)pyrazolo[4,3-d]-pyrimidine-7-one

The compound was prepared as in Example 6A using 1.97 g of 1,3-dimethyl-5-cyanopyrazole-4-N-(3-methoxyphenyl)carboxamide, 0.44 g sodium hydroxide and 1.7 ml 30% $H_2O_2$, mp 263°-264° C.

Analysis as $C_{14}H_{14}N_4O_2$: Calcd: C, 62.21; H, 5.22; N, 20.73; Found: C, 62.29; H, 5.19; N, 20.68

The starting material was prepared as in Example 6A using the corresponding acid chloride, mp 149°-150° C.

EXAMPLE 25

1,3-Dimethyl-5(2-pyrazolo[4,3-d]pyrimidine-7-one

The bis-amdie as prepared as in Example 4 using 2.0 g of 1,3-dimethyl-4-aminopyrazole-5-carboxamide, 1.84 g picolinic acid chloride and 3.03 g triethylamine, mp 193°-194° C. This was cyclized and purified as in Example 4 to give the product, mp 278°-280° C.

Analysis as $C_{12}H_{11}N_4O$: Calcd: C, 59.74; H, 4.60; N, 29.03; Found: C, 59.46; H, 4.58; N, 29.08

STARTING MATERIALS

Scheme I 1,3-Dimethyl-4-nitro-pyrazole-5-carboxylic acid

One-hundred twelve g concentrated sulfuric acid is added to 42 ml 90% nitric acid at 70°-80° C., 39 g of 1,3-dimethylpyrazole-5-carboxylic acid is added in portions over one hour such that the temperature does not go over 90° C. After 2.5 hours the reaction mixture is cooled and poured over ice. The resulting percipitate was filtered, dried, and recrystallized in ethanol, mp 141°-142° C.

1,3-Dimethyl-4-nitropyrazole-5-carboxamide

Forty g of 1,3-dimethyl-4-nitropyrazole-5-carboxylic acid was stirred with 200 ml thionyl chloride at reflux for 3.5 hours. The excess thionyl chloride was distilled away under reduced pressure. The resulting oil was dissolved in acetone and added to icy ammonium hydroxide with stirring. The resulting percipitate was filtered and dried to give the product, mp 154°-158° C.

1,3-Dimethyl-4-aminopyrazole-5-carboxamide

Fifty g of 1,3-dimethyl-4-nitropyrazole-5-carboxamide dissolved in methanol, 2 g 50% aqueous Raney nickel added, was reduced under a hydrogen atmosphere until a 8.15 pound drop in pressure noted. The reaction mixture was filtered, the filtrate concentrated, and the crude material recrystallized in ethyl acetate to yield the product, mp. 154°-155° C.

Scheme II 1,3-Dimethyl-4-nitro-5-cyano-pyrazole

Fifty-five g of 1,3-dimethyl-4-nitro-5-chloropyrazole was dissolved in 400 ml acetonitrile and 17.45 g potassium cyanide added, followed by 0.5 g potassium iodide and 5 ml DMF. The mixture was refluxed for 22 hours, then cooled, and filtered. The filtrate was concentrated under reduced pressure, then added to stirred water. The resulting percipitate was collected, dried, and recyrstallized in isopropanol. mp, 85°-87° C. A second recrystallization again in ethanol gave the product having increased purity, mp 96°-98° C.

1,3-Dimethyl-4-amino-5-cyanopyrazole

Two-hundred and seventy-two g of 1,3-dimethyl-4-nitro-5-cyano-pyrazole was subjected to catalytic hydrogenation in methanol using a Raney nickel catalyst. The catalyst was filtered away and the filtrate concentrated. The product solidified, mp 109°-111° C.

For Schemes I and II

1-Ethyl-3-methyl-pyrazole compounds were prepared in a strictly analogous manner to the 1,3-dimethyl compounds.

EXAMPLE 26

1,3-Dimethyl-5-(2-aminophenyl)pyrazolo[4,3-d]pyrimidine-7-one

The compound was prepared as in Example 11 using 1,3-dimethyl-5-(2-nitrophenyl)pyrazolo[4,3-d]pyrimidine-7-one. It was purified by recrystallizing from ethanol, mp 290°-292° C.

Analysis as: $C_{13}H_{13}N_5O$: Calcd: C, 61.17; H, 5.13; N, 27.43; Found: C, 60.77; H, 5.12, N, 27.13

Starting Material for Example 26

1,3-Dimethyl-5-(2-nitrophenyl)pyrazolo[4,3-d]pyrimidine-7-one

The starting bis-amide was prepared as in Example 6A using 10 g of 1,3-dimethyl-4-aminopyrazole-5-carboxamide, 12 g of 2-nitrobenzoylchloride, and 6.55 g of triethylamine, mp 289°-294° C. It was cyclized as in Example 6A using 1.29 g sodium hydroxide and 4.62 ml of 30% hydrogen peroxide. The crude product was used in the preparation of 1,3-dimethyl-5-(2-aminophenyl)pyrazolo[4,3-d]pyrimidine-7-one above.

I claim:

1. A compound of the formula

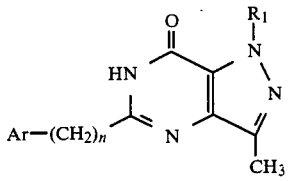

wherein $R_1$ is lower alkyl of from one to six carbons, inclusive, lower alkenyl of from two to six carbons, inclusive, lower hydroxyalkyl of from one to six carbons, inclusive, lower hydroxyalkenyl of from two to six carbons, inclusive, dimethylaminoethyl or lower amino alkenyl of from two to six carbons, inclusive; n is 0-4; and Ar is

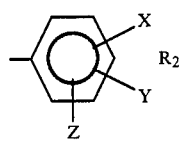

or 2, 3, or 4-pyridyl, wherein X, Y, and Z are independently (1) hydrogen; (2) lower alkyl of from one to six carbons, inclusive; (3) halogen; (4) hydroxyl; (5) lower alkoxy of from one to six carbons, inclusive; (6) nitro; (7) amino; (8) NR'R" wherein R' and R" are each independently (a) hydrogen or (b) lower alkyl of from one to six carbons, inclusive, optionally substituted by (i) amino, (ii) morpholino or (iii) cycloalkyl of from five to seven carbons, inclusive; (9) sulfo; or (10) —SO$_2$NR'R" wherein R' and R" are as defined above with the proviso that not all of X, Y, and Z can be nitro, amino, or NR'R" at once; and pharmaceutically acceptable salts thereof.

2. A compound of claim 1 wherein Ar is R$_2$ and n is 0.

3. A compound of claim 1 wherein Ar is 2-, 3-, or 4-pyridyl.

4. A compound of claim 1 wherein Ar is R$_2$, R$_1$ is methyl and n is 1.

5. A compound of claim 2 wherein the embodiment is 1-ethyl-3-methyl-5-phenylpyrazolo[4,3-d]pyrimidine-7-one.

6. A compound of claim 3 wherein the embodiment is 1,3-dimethyl-5-(3-pyridyl)pyrazolo[4,3-d]pyrimidine-7-one.

7. A compound of claim 2 wherein the embodiment is 1,3-dimethyl-5-phenylprazolo[4,3-d]pyrimidine-7-one.

8. A compound of claim 4 wherein the embodiment is 1,3-dimethyl-5-benzylpyrazolo[4,3-d]pyrimidine-7-one.

9. A compound of claim 2 wherein the embodiment is 1,3-dimethyl-5-(4-chlorophenyl)pyrazolo[4,3-d]pyrimidine-7-one.

10. A compound of claim 2 wherein the embodiment is 1,3-dimethyl-5-(4-methylphenyl)pyrazolo[4,3-d]pyrimidine-7-one.

11. A compound of claim 2 wherein the embodiment is 1,3-dimethyl-5-(4-nitrophenyl)pyrazolo[4,3-d]pyrimidine-7-one.

12. A compound of claim 2 wherein the embodiment is 1,3-dimethyl-5-(4-trifluoromethylphenyl)-pyrazolo[4,3-d]pyrimidine.

13. A compound of claim 2 wherein the embodiment is 1,3-dimethyl-5-(4-aminophenyl)pyrazolo[4,3-d]pyrimidine-7-one.

14. A compound of claim 2 wherein the embodiment is 1,3-dimethyl-5-(3-aminophenyl)pyrazolo[4,3-d]pyrimidine-7-one.

15. A compound of claim 2 wherein the embodiment is 1,3-dimethyl-5-(3-nitrophenyl)pyrazolo[4,3-d]pyrimidine-7-one.

16. A compound of claim 2 wherein the embodiment is 1,3-dimethyl-5-(2-methoxyphenyl)pyrazolo[4,3-d]pyrimidine-7-one.

17. A compound of claim 2 wherein the embodiment is 1,3-dimethyl-5-(3,4-dichlorophenyl)pyrazolo[4,3-d]pyrimidine-7-one.

18. A compound of claim 2 wherein the embodiment is 1,3-dimethyl-5-(3,4-dimethoxyphenyl)pyrazolo[4,3-d]pyrimidine-7-one.

19. A compound of claim 2 wherein the embodiment is 1,3-dimethyl-5-(2,4-dimethoxyphenyl)pyrazolo[4,3-d]pyrimidine-7-one.

20. A compound of claim 2 wherein the embodiment is 1,3-dimethyl-5-(2-nitro-4-chlorophenyl)pyrazolo[4,3-d]pyrimidine-7-one.

21. A compound of claim 2 wherein the embodiment is 1,3-dimethyl-5-(2-amino-4-chlorophenyl)-pyrazolo[4,3-d]pyrimidine-7-one.

22. A compound of claim 2 wherein the embodiment is 1,3-dimethyl-5-(4-sulfophenyl)pyrazolo[4,3-d]pyrimidine-7-one.

23. A compound of claim 4 wherein the embodiment is 1-ethyl-3-methyl-5-benzylpyrazolo[4,3-d]pyrimidine-7-one.

24. A compound of claim 2 wherein the embodiment is 1,3-dimethyl-5-(3,5-dimethoxyphenyl)pyrazolo[4,3-d]pyrimidine-7-one.

25. A compound of claim 2 wherein the embodiment is 1,3-dimethyl-5-(3-methoxyphenyl)pyrazolo[4,3-d]pyrimidine-7-one.

26. A compound of claim 3 wherein the embodiment is 1,3-dimethyl-5-(2-pyridyl)pyrazolo[4,3-d]pyrimidine-7-one.

27. A pharmaceutical composition for treating cardiac insufficiency comprising a cardiotonic effective amount of a compound according to claim 1 in admixture with a pharmaceutically acceptable carrier.

28. A method for treating cardiac insufficiency in a mammal suffering therefrom comprising administering to such mammal a compound as claimed in claim 1 in unit dosage form.

29. A compound of claim 3 wherein the embodiment is 1-ethyl-3-methyl-5-(4-pyridyl)pyrazolo[4,3-d]pyrimidine-7-one.

30. A compound of claim 3 wherein the embodiment is 1,3-dimethyl-5-(4-pyridyl)pyrazolo[4,3-d]pyrimidine-7-one.

31. A compound of claim 2 wherein the embodiment is 4-(6,7-dihydro-1,3-dimethyl-7oxo-1H-pyrazolol[4,3-d]pyrimidin-5-yl)-N-[2-(dimethylamino)ethyl]benzenesulfonamide.

* * * * *